United States Patent
Werle et al.

(10) Patent No.: US 8,114,992 B2
(45) Date of Patent: Feb. 14, 2012

(54) METHOD FOR THE PRODUCTION OF 2,4,6-TRIMERCAPTO-1,3,5-TRIAZINE

(75) Inventors: Peter Werle, Gelnhausen (DE); Martin Trageser, Gelnhausen (DE); Michael Beck, Hanau (DE)

(73) Assignee: Evonik Degussa GmbH, Essen (DE)

( * ) Notice: Subject to any disclaimer, the term of this patent is extended or adjusted under 35 U.S.C. 154(b) by 843 days.

(21) Appl. No.: 11/996,173

(22) PCT Filed: Jul. 3, 2006

(86) PCT No.: PCT/EP2006/063795
§ 371 (c)(1),
(2), (4) Date: Jul. 18, 2008

(87) PCT Pub. No.: WO2007/017314
PCT Pub. Date: Feb. 15, 2007

(65) Prior Publication Data
US 2008/0293935 A1 Nov. 27, 2008

(30) Foreign Application Priority Data
Aug. 4, 2005 (DE) .......................... 10 2005 036 693

(51) Int. Cl.
*C07D 251/38* (2006.01)

(52) U.S. Cl. ..................................................... 544/219
(58) Field of Classification Search ................... 544/219
See application file for complete search history.

(56) References Cited

U.S. PATENT DOCUMENTS

| | | | |
|---|---|---|---|
| 4,822,496 A | 4/1989 | Griffiths et al. |
| 4,849,517 A | 7/1989 | Weber et al. |
| 5,006,654 A | 4/1991 | Ludwig et al. |
| 5,075,444 A | 12/1991 | Hentschel et al. |
| 5,258,515 A | 11/1993 | Hentschel et al. |
| 6,652,986 B2 | 11/2003 | Peldszus et al. |
| 2008/0251758 A1 | 10/2008 | Kirchhoff et al. |

OTHER PUBLICATIONS

U.S. Appl. No. 07/569,137, filed Aug. 17, 1990, Hentschel, et al.
U.S. Appl. No. 12/993,705, filed Nov. 19, 2010, Grimmer, et al.

*Primary Examiner* — Venkataraman Balasubramanian
(74) *Attorney, Agent, or Firm* — Oblon, Spivak, McClelland, Maier & Neustadt, L.L.P.

(57) ABSTRACT

The present invention is directed towards a method for the production of 2,4,6-trimercapto-1,3,5-triazine (TMT-$H_3$). In particular, the method of the subject matter relates to the operation of acidifying the salts of 2,4,6-trimercapto-1,3,5-triazine in aqueous solution and in a defined pH range.

8 Claims, No Drawings

METHOD FOR THE PRODUCTION OF 2,4,6-TRIMERCAPTO-1,3,5-TRIAZINE

The present invention is directed towards a method for the production of 2,4,6-trimercapto-1,3,5-triazine (TMT-$H_3$). In particular, the method of the subject matter relates to the operation of acidifying the salts of 2,4,6-trimercapto-1,3,5-triazine (TMT) in aqueous solution and in a defined pH range.

2,4,6-Trimercapto-1,3,5-triazine [CAS-No. 638-16-4], whose readily water-soluble trisodium salt [CAS-No. 17766-26-6] has already been in industrial use for a relatively long time for purifying heavy metal-containing wastewater and exhaust gas streams, can be used in the form of the free acid in various ways in the rubber industry sector. Especially epichlorohydrin rubbers and their copolymers with, e.g. ethylene oxide (what are termed ECO rubbers), which are crosslinked by ethylene thiourea to improve the physical and chemical properties, can mature to form an important field of use. This is because this crosslinking has to date additionally required lead compounds such as red lead or lead phosphate which bind the hydrochloric acid formed in vulcanization.

The environmental pollution due to lead and also fundamental considerations on the toxicity of ethylene thiourea (ETU) have lead to the fact that lead is no longer being used at least in the car manufacturing sector. An effective substitute for the ETU/Pb system has proved to be TMT-$H_3$, with which, if appropriate, in addition to activators, nontoxic calcium or magnesium compounds can be used.

Methods for the production of TMT-$H_3$ are described in a plurality of publications.

In addition to methods which use ammonium thiocyanate or other salts of thiocyanic acid as starting material and obtain the TMT-$H_3$ by cyclotrimerization in the strongly acidic system, most processes start from cyanuric chloride which is reacted with salts of hydrosulphuric acid, if appropriate in the presence of a lye.

For instance, according to CS 230344, cyanuric chloride is hydrolysed in aqueous acetone with concentrated $Na_2S$ solution at 80° C. for 4 h and subsequently acidified. The yield is said to be 80%.

CS 265150 describes the reaction of a cyanuric chloride suspension with an NaSH/$Na_2S$/$Na_2CO_3$ mixture and acidification with sulphuric acid (yield 90%, purity 95%).

In U.S. Pat. No. 5,563,267, trialkali metal and triammonium salts of TMT-$H_3$ are produced, the free acid being precipitated out by addition of NaSH to a solution of cyanuric chloride in acetone. In addition, the product is acidified with hydrochloric acid.

Diagram 1:

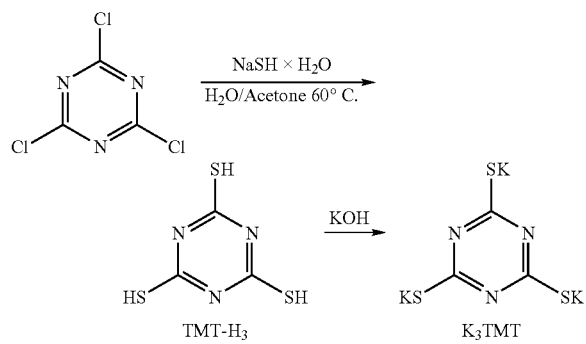

Our work has found that the trimercaptotriazine synthesis which actually can be carried out according to the diagram 2:

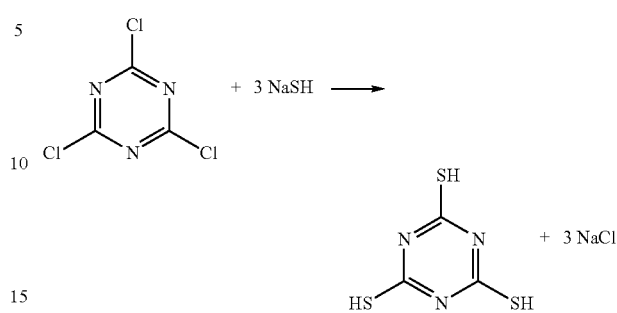

leads to products which do not satisfy the requirements of the rubber industry for a TMT-$H_3$ crosslinker. The purity is <95%, alkaline solutions are turbid and the odour is strong and untypical. Apparently, in this direct synthesis, side reactions occur such as hydroxyl derivatives and bridged systems. The nature of the impurities is not yet known in detail. A successful synthesis of a pure TMT-$H_3$ proceeds via the formation of water-soluble salts of TMT, from which the pure TMT-$H_3$ is then precipitated by acidification:

Diagram 3:

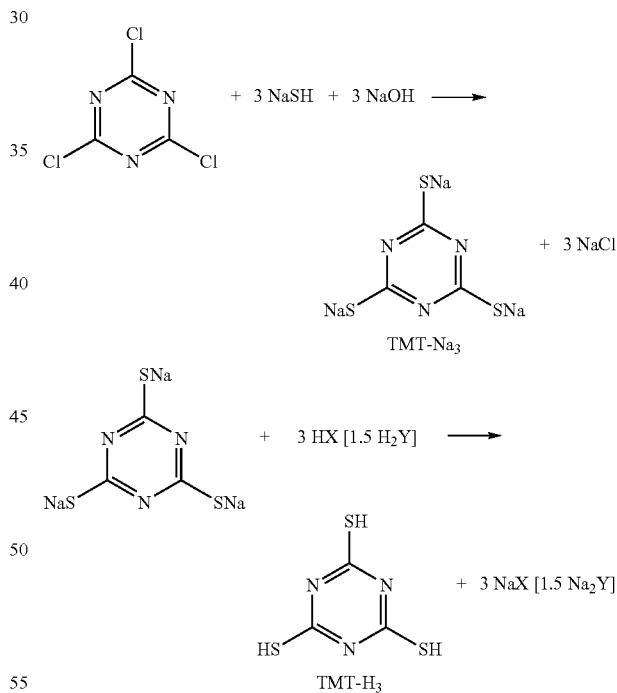

X = Cl, Br Y = $SO_4$

Preferably, disodium or trisodium salt is used. A method for the production of the trisalt is described in DE 3729029.

Customarily, a TMT-$Na_3$ solution (pH approximately 12) is admixed, with stirring, with a strong acid until a pH<2 is present and as a result acid precipitation occurs. In this method, which is also occasionally reported in the abovementioned patents, a fundamental difficulty occurs which makes carrying it out industrially virtually impossible in practice.

Formation of the free acid on acidification proceeds with intermediate formation of the following intermediates:

Diagram 4:

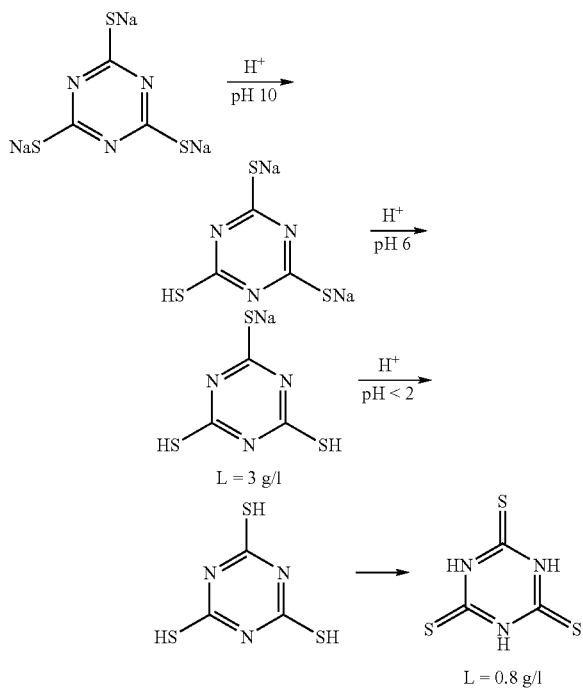

Therefore, from pH 6 the monosodium salt precipitates out which, at pH<2, is probably converted in a solid/solid reaction to give the free acid.

In this customary procedure, it emerges that the reaction batch, with increasing solids precipitation, becomes increasingly more difficult to mix, since the precipitates cannot be drawn into the stirring zone and thus homogeneous mixing cannot be achieved. As a result of the poor mixing, the Na salt can thus not be completely converted to the free acid. A consequence is that a TMT-H$_3$ obtained by filtration according to this method still has a high ash content. In addition, the precipitated product proves to be extremely finely divided, so that very long filtration times and especially also wash times are required in order to remove the dissolved sodium salts (e.g. NaCl or Na$_2$SO$_4$). This results in very low space-time yields and thus high production costs.

It was therefore an object of the present invention to specify a further method which is superior in economic and ecological aspects to the method of the prior art and helps to overcome the above-described disadvantages of the known methods.

This object is achieved according to the claims.

As a result of the fact that, in a method for the production of 2,4,6-trimercapto-1,3,5-triazine by acidification of a solution of the corresponding salts of 2,4,6-trimercapto-1,3,5-triazine in aqueous solution, while the operation of acidification maintains a pH range from 1.5 to 2.5, extremely surprisingly, but no less advantageously, the solution of the object of interest is achieved. The quality of the 2,4,6-trimercapto-1,3,5-triazine precipitate obtained by this method is sufficient to establish substantially shorter filtration times and wash and drying times in the method and thus to arrive at an economically more expedient method.

In a preferred embodiment, in the inventive method a procedure is followed such that an aqueous solution adjusted to a pH of approximately 2 is charged and to this is added, with pH control (e.g. by adding acid), a solution of the corresponding salts of 2,4,6-trimercapto-1,3,5-triazine in aqueous solution. In this case, those skilled in the art are free to choose how the pH can be controlled. Advantageously, this can be achieved by the fact that, simultaneously with the addition of the solution of the corresponding salts of 2,4,6-trimercapto-1,3,5-triazine, an acidic aqueous solution, which is preferably produced from an inorganic acid and water (see below), is added in such a manner that the above-specified pH range can be maintained. The control can proceed using means known to those skilled in the art, for example using a pH electrode.

Particularly advantageous is the fact that the acidification of the corresponding salts of 2,4,6-trimercapto-1,3,5-triazine proceeds in a pH range from 1.75 to 2.25, preferably 1.75 to 2.1.

Further advantageous is an inventive method in which, during the acidification of the salts of 2,4,6-trimercapto-1,3,5-triazine, 1,3,5-triazine, small amounts of an organic high-molecular-weight polyacrylamide are present. Such high-molecular-weight substances are sufficiently known to those skilled in the art and are commercially available (Praestol and Praestol 2500).

The inventive method is preferably carried out at a temperature of 40-70° C., more preferably at 50-65° C., and very particularly preferably at 55-62° C. The concentration of the salts used of 2,4,6-trimercapto-1,3,5-triazine is to be such that, in the feed solution, a concentration of 0.80-1.45 mol/l, preferably 0.90-1.25 mol/l, and very particularly preferably 0.95-1.20 mol/l, is present.

The present invention describes an industrial method for producing, from the readily water-soluble trisodium salt of TMT (~300 g/l) or disodium salt (~750 g/l), the practically water-insoluble acid (~0.8 g/l). Surprisingly, the TMT-H$_3$ suspension which has been precipitated out according to the invention remains of low viscosity. Since over the entire method duration no pH change occurs, no significant increase in viscosity is measured towards the end of addition either. The free acid is produced in pure form and, because of the constant pH condition, without contamination by the monosodium salt. In addition, it has been found that the filterability is significantly improved. In addition, this can be improved if an organic high-molecular-weight polyacrylamide is added (as 0.1-0.5% strength aqueous solution) in amounts of 0.01 to 1 g/l, preferably 0.1 to 0.4 g/l, of reaction solution.

The inventive method produces, in a particularly simple manner, pure 2,4,6-trimercapto-1,3,5-triazine having contents of >99% and ash contents of <0.1%, which have been unexpected from the outset.

Acidification or production of acidic aqueous solutions preferably proceeds using strong organic or inorganic acids. It is advantageous to use strong inorganic acids selected from the group consisting of hydrochloric acid, sulphuric acid, phosphoric acid, but strong organic acids can also be used, e.g. trifluoroacetic acid, p-toluenesulphonic acid and the like.

The examples hereinafter are intended to explain the inventive method in more detail; the comparative example represents the delimitation from the prior art.

COMPARATIVE EXAMPLE

To a precharged solution consisting of
137.5 g of trimercaptotriazine trisodium salt
molecular weight 243.2=0.565 mol
in
412.5 g of distilled water (equivalent to ~25% strength solution)
are added, in the course of 30 min, with stirring at room temperature
207.6 g of sulphuric acid 40% molecular weight 98.07=0.847 mol,
the reaction temperature increasing to 40-45° C.

The TMT-H₃ formed precipitates out in very finely divided form, the batch becomes extremely thick in the last third of addition, aluminous [cream-cheese-like] and can scarcely be stirred any longer. 1½ h postreaction. Final pH of the suspension=1.9

The product is filtered off by suction through a Ø 16 cm vacuum filter, filtration time: 3 h a pasty, runny filtercake being obtained.

Subsequent washing salt-free with distilled water required 6-8 h.

The moist product is dried at 105° C. in a vacuum cabinet.

| Yield: | 92.6 g TMT-H3 molecular weight 177.2 equivalent to 92.50% of theory. |
|---|---|
| Ash content: | 1.7% |

EXAMPLE NO. 1

To 130 g of precharged distilled water, adjusted to pH 2.0 by addition of a little hydrochloric acid, in the course of 60 min, 550 g of a 25% strength solution of trimercaptotriazine trisodium salt in water at a temperature of 40-50° C., to which 21 g of a 0.43% strength aqueous Praestol 2500 solution have been added, and also 170 g of 37% strength hydrochloric acid are added simultaneously, so that in the system a pH of 1.8-2.0 is always present. The reaction temperature increases in the course of this to approximately 50-60° C. and the TMT-H₃ forming immediately precipitates out in flocculent, constantly very readily stirrable form. 1 h postreaction at 60° C. and pH 1.9-2.0. Filtration using suction through a Ø 16 cm porcelain vacuum filter, filtration time: 20 sec.

Wash salt-free using distilled water, time: 30 min and dry in vacuum at 105° C.

| Yield: | 98.5 g of TMT-H₃ equivalent to 98.4% of theory molecular weight 177.2 |
|---|---|
| Ash content: | <<0.1% |
| TMT-H₃ content: | 99.4% |

EXAMPLE NO. 2

A 25% strength solution is produced from 250 kg of TMT-55 (trimercaptotriazine trisodium salt) and 300 kg of deionized water at T=60° C., to this solution are added 25 kg of Praestol 2500 solution [~0.4% strength] and the mixture is homogenized. In a suitable reaction vessel, 150 kg of deionized water (adjusted to pH 2.0 using $H_2SO_4$) are then charged and, with stirring, and pH measurement, 210 kg of sulphuric acid 40% strength and the TMT solution are pumped in simultaneously in the course of 60-90 min, so that a pH of approximately 2 is always present. 2 h postreaction at approximately 60° C., pH 1.7-1.9. Filter and wash salt-free with deionized water, dry.

| Yield: | 100 kg of TMT-H₃ equivalent to 99.8% of theory molecular weight 177.2 |
|---|---|
| TMT-H₃ content: | 99.6% |
| Ash content: | <<0.1% |

The invention claimed is:

1. A method for the production of 2,4,6-trimercapto-1,3,5-triazine comprising acidifying, in the presence of an organic high molecular weight polyacrylamide, an aqueous solution of one or more salts of 2,4,6-trimercapto-1,3,5-triazine,
    wherein a pH range of 1.5 to 2.5 is maintained during the acidifying.

2. The method according to claim 1,
    wherein the acidifying comprises adjusting an aqueous solution adjusted to a pH of approximately 2 and then adding, with pH control, the aqueous solution of one or more salts of 2,4,6-trimercapto-1,3,5-triazine.

3. The method according to claim 1,
    wherein the acidifying is performed in a range of 1.75 to 2.25.

4. The method according to claim 1, wherein the organic high molecular weight polyacrylamide is added as a 0.1 to 0.5% strength aqueous solution in an amount of 0.01 to 1 g/l of reaction solution.

5. The method according to claim 1, wherein said method is carried out at a temperature of from 40° C. to 70° C.

6. The method according to claim 1, wherein the aqueous solution of one or more salts of 2,4,6-trimercapto-1,3,5-triazine contains said salts in an amount of 0.80 to 1.45 mol/l.

7. The method according to claim 1, wherein the acidifying occurs via the addition of one or more acids selected from the group consisting of hydrochloric acid, sulphuric acid, phosphoric acid, trifluoroacetic acid and p-toluenesulphonic acid.

8. The method according to claim 1, wherein the 2,4,6-trimercapto-1,3,5-triazine produced according to said method has a content of 2,4,6-trimercapto-1,3,5-triazine of greater than 99% and an ash content of less than 0.1%.

* * * * *